United States Patent

Sparer et al.

[11] Patent Number: 6,159,240
[45] Date of Patent: Dec. 12, 2000

[54] RIGID ANNULOPLASTY DEVICE THAT BECOMES COMPLIANT AFTER IMPLANTATION

[75] Inventors: Randall V. Sparer, Andover; Darrel F. Untereker, Oak Grove; Elizabeth A. Ebner, Dayton; Thomas P. Grailer, Ramsey; Brett R. Vegoe, Coon Rapids, all of Minn.; Hong S. Shim, Santa Ana, Calif.; Carlos M. G. Duran, Missoula, Mont.

[73] Assignee: Medtronic, Inc., Minneapolis, Minn.

[21] Appl. No.: 09/144,374

[22] Filed: Aug. 31, 1998

[51] Int. Cl.[7] .................................................... A61F 2/24
[52] U.S. Cl. ............................................................ 623/2.36
[58] Field of Search ............................. 623/2, 900, 2.36, 623/2.37

[56] References Cited

U.S. PATENT DOCUMENTS

| | | |
|---|---|---|
| 5,011,481 | 4/1991 | Myers et al. . |
| 5,041,130 | 8/1991 | Cosgrove . |
| 5,376,112 | 12/1994 | Duran .................................. 623/2.1 X |
| 5,716,397 | 2/1998 | Myers . |
| 5,728,152 | 3/1998 | Mirsch, II et al. . |

FOREIGN PATENT DOCUMENTS

| | | | |
|---|---|---|---|
| 97/16135 | 5/1997 | WIPO | ......................................... 623/2 |
| 97/46177 | 12/1997 | WIPO | ......................................... 623/2 |

OTHER PUBLICATIONS

"Carpentier–Edwards® Prosthetic Rings Models 4500 and 4400 for Tricuspid and Mitral Valvuloplasty," Baxter Healthcare Corp., pp. 1–8 (1991).

"Cosgrove–Edwards™ Annuloplasty System Mitral Model 4600 with Handle/Lanyard for Mitral Valvuloplasty," Baxter Healthcare Corp., pp. 1–6 (1994).

"Duran Flexible Annuloplasty Ring," Medtronic, cover page, pp. 1–8.

*Primary Examiner*—David H. Willse
*Attorney, Agent, or Firm*—Thomas F. Woods; Harold R. Patton

[57] ABSTRACT

A band-shaped annuloplasty device (e.g., C- or D-shaped ring) that is relatively rigid during handling and implantation and becomes relatively complaint after implantation. Preferably, the device includes a core material that softens after implantation.

38 Claims, 2 Drawing Sheets

RIGID ANNULOPLASTY DEVICE THAT BECOMES COMPLIANT AFTER IMPLANTATION

FIELD OF THE INVENTION

This invention relates to annuloplasty devices, such as rings or bands, for use in heart valve surgery, and more particularly to a rigid annuloplasty device that becomes compliant after implantation.

BACKGROUND OF THE INVENTION

Human heart valves, such as the mitral and tricuspid valves are sometimes damaged by diseases or by aging which cause problems with the proper function of the leaflets and/or the sub-valvular apparatus attached to the leaflets. Often, degenerative disease causes the valve annulus to enlarge to the point where the leaflets attached to it cannot fully close. This inability to completely close, a condition called valve incompetence, eventually requires surgical correction either by valve repair procedures or by valve replacement. In the former, also called valvular annuloplasty, various types of ring-shaped devices or bands fashioned from biocompatible cloth-like materials are sewn to the distended orifice (i.e., annulus of the valve). By properly sizing and devising the annuloplasty ring or band, the surgeon can restore the valve annulus to its normal, undilated, circumference.

Annuloplasty rings or bands are typically of two types, either completely flexible or stiff and comparatively rigid. An example of the former is the Duran Ring or the Cosgrove Band, while an example of the latter is the Carpentier Ring.

The Carpentier Ring consists of a split D-shaped titanium ring completely covered with cloth. The ring is somewhat stiff yet resiliently deformable and is not intended to be removable from the cloth covering. This ring is particularly useful in the repair of heart valves that have lost annular elasticity from, e.g., the chronic effects on the mitral valve of rheumatic fever. Due to their permanent rigidity, the Carpentier Rings lie flat and maintain their D-shape during handling by the surgeon at time of implantation. Many surgeons prefer to use the Carpentier Ring because it is somewhat easier to implant; in particular, easier to achieve a visually aesthetic result with no ring buckling. In addition, it is also easier for the surgeon to test the functionality of the valve immediately after the installation of the repair ring. Although the Carpentier Ring's rigid D-shape is claimed to enhance the competence of the repaired valve, the rigidity also impedes the beneficial flexing movements of the native annulus during the cardiac cycle.

The other major type of annuloplasty ring or band is exemplified by the totally flexible Duran Ring or the Cosgrove Band. These devices consist of a soft core of silicone rubber impregnated with a radiopaque salt (e.g., barium sulfate) completely enclosed by a sheath of biocompatible cloth (e.g., polyester fabric). These devices are completely flexible and useful in the repair of heart valves whose annuli have become enlarged in diameter but are not stiffened and inflexible. Because of its flexibility, the Duran Ring is supported during implantation by a holder which is subsequently removed before tie-off of the sutures, as shown in U.S. Pat. No. 5,011,481 (Myers et al.). One problem with this approach is that the holder does not completely restrain the entire circumference of the ring and does not prevent the flexible ring from bunching or forming pleats as the sutures are tied off. The Cosgrove Band, like the Duran Ring, is totally flexible; however, bunching of the Cosgrove Band is prevented by the mounting of the device on a rigid support, as shown in U.S. Pat. No. 5,041,130 (Cosgrove et al.), which is subsequently removed after the sutures are tied off. Neither the Duran Ring nor the Cosgrove Band can be tested for competence in the ideal systolic shape as can the rigid Carpentier Ring.

Hybrids of the foregoing types of rings have also been proposed, as for example the Sculptor ring in which the anterior segment (which corresponds to the intertrigone area) is rigid but the posterior segment is totally flexible and also fitted with drawstrings to finely adjust its diameter. Although this complex ring can be used in the same circumstances as Duran Ring, it mitigates but does not overcome the handling difficulties associated with flexible rings.

To overcome the deficiencies of the above-described ring/band structures, it would be ideal for an annuloplasty device to be stiff during handling and implantation, but then become flexible after implantation. One such device is disclosed in U.S. Pat. No. 5,716,397 (Myers). In this device, there is a fully flexible annuloplasty ring that is temporarily stiffened during implantation by inserting a withdrawable stiffening wire into a lumen of the ring, which is able to hold the stiffener prior to and during insertion. The stiffening wire includes a portion extending out of the lumen which can be pulled to withdraw it once the device has been implanted. There is still a need, however, for other devices that are generally stiff or rigid during handling and implantation but become more flexible after implantation.

The following documents disclose information about annuloplasty devices.

TABLE 1

| U.S. Pat. No. | Inventor Name | Date Issued |
|---|---|---|
| 5,011,481 | Myers et al. | April 30, 1991 |
| 5,041,130 | Cosgrove | August 20, 1991 |
| 5,716,397 | Myers | February 10, 1998 |
| 5,728,152 | Mirsch, II et al. | March 17, 1998 |

Other Document

"Carpentier-Edwards ® Prosthetic Rings Models 4500 adn 4400 for Tricuspid and Mitral Valvuloplasty," Baxter Healthcare Corp., pgs. 1–8 (1/1991).
"Cosgrove-Edwards ™ Annuloplasty System Mitral Model 4600 with Handle/Lanyard for Mitral Valvuloplasty," Baxter Healthcare Corp., pgs. 1–6 (8/1994).
"DURAN Flexible Annuloplasty Ring," Medtronic, cover page.
"DURAN Flexible Annuloplasty Ring," Medtronic, pgs. 1–8.

All patent and nonpatent documents listed in Table 1 are hereby incorporated by reference herein in their respective entireties. As those of ordinary skill in the art will appreciate upon reading the Summary of the Invention, Detailed Description of Preferred Embodiments, and Claims set forth below, many of the systems, devices, and methods disclosed in these documents may be modified advantageously by using the teachings of the present invention.

SUMMARY OF THE INVENTION

The present invention provides an annuloplasty device for implantation into a heart of a patient, comprising a band-shaped member having an initial modulus of elasticity of about 145 kpsi (1 GPa) or more, and a final modulus of elasticity of about 14,500 psi (100 MPa) or less after immersion in a biological environment (e.g., implantation in the body of a human patient). Preferably, the final modulus of elasticity is reached after immersion in a biological environment for no more than about 7 days, and more preferably, for no more than about 3 days.

The band-shaped member can be in any of a variety of shapes as long as it is suitable for use in an annuloplasty device. For example, it can be in the form of an open ring (e.g., C-shaped) or a closed ring (e.g., D-shaped). Thus, it can be discontinuous or substantially continuous.

Typically, the band-shaped member comprises a structural component and a flexibilizing component, which may be the same or different. The structural component is the structural means for providing support (physical integrity) to the device and the flexibilizing component is the flexibilizing means for providing a change in modulus of elasticity after immersion in a biological environment.

In one embodiment, the flexibilizing component is impregnated in the structural component. Alternatively, the structural component has an external surface and the flexibilizing component is coated on at least a portion of the external surface of the structural component. Preferably, the flexibilizing component is coated on the entire external surface of the structural component. In yet another embodiment, the band-shaped member comprises a core flexibilizing component and a structural component that completely envelopes the core flexibilizing component.

The flexibilizing component can be made of a variety of materials, such as poly(vinyl alcohol-co-vinyl acetate) or poly(vinyl pyrrolidone), for example. It can be in a variety of shapes, such as tubes or rods, for example. The flexibilizing component preferably changes modulus in a biological environment as a result of dissolution, biodegradation, plasticization, or phase transition.

In one embodiment, the present invention provides an annuloplasty device for implantation into a heart of a patient, comprising a band-shaped member having an initial modulus of elasticity of about 1 GPa or more, and a final modulus of elasticity of about 100 MPa or less after immersion in a biological environment; wherein the band-shaped member comprises a structural component and a flexibilizing component comprising poly(vinyl alcohol-co-vinyl acetate). The structural component preferably completely envelopes the flexibilizing component.

In another embodiment, the present invention provides an annuloplasty device for implantation into a heart of a patient, comprising a band-shaped member having an initial modulus of elasticity of about 1 GPa or more, and a final modulus of elasticity of about 100 MPa or less after immersion in a biological environment for no more than about 7 days; wherein the band-shaped member comprises a core material that softens after immersion in the biological environment.

DESCRIPTION OF PREFERRED EMBODIMENTS

Figure 1:
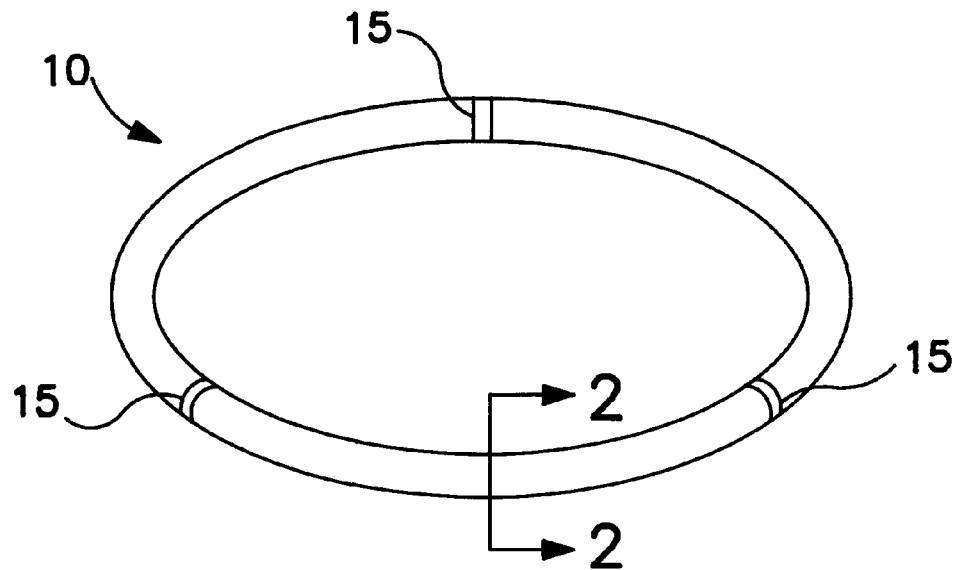
FIG. 1 (prior art) is a plan view of a conventional Duran Ring.
Figure 2:
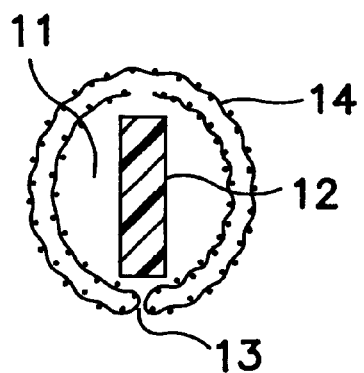
FIG. 2 (prior art) is a section along line 2—2 of FIG. 1.

FIGS. 1 and 2 illustrate a conventional Duran Ring construction. Like the Cosgrove Band, the Duran Ring 10 has a lumen 11 containing a generally rectangular inner core 12 of radio-opaque silicone rubber which is radially completely flexible. The radiopacity of the core 12 allows the presence of the device to be monitored after completion of the implant surgery. The core 12 is completely enclosed by a sheath 14 of biocompatible cloth. The sheath 14 is made by folding a cloth sheet around the core 12 and sewing the folded ends together at 13. The combination of the core 12 and sheath 14 result in a ring which is completely flexible yet essentially nonextensible. This property allows the annuloplasty ring or band, when implanted in the heart, to prevent the valve annulus from becoming distended, without significantly impeding the natural motion of the annulus. The ring 10 has three trigone markers 15 sewn thereon at 120° intervals to assist the surgeon in the placement of sutures.

After implantation, the final confirmation of the Duran Ring is roughly planar, and somewhat D shaped, although the exact shape of the natural orifice is different in the systolic (closed) and the diastolic (open) positions. The ability of the Duran Ring to easily flex to accommodate the orifice shape during the cardiac cycle is one of its major advantages. Another advantage of the Duran Ring is a reduced chance of dehiscence (i.e., splitting from the tissue).

One of the disadvantages of the Duran Ring is that it needs to be supported in its proper shape during the implantation procedure. This is typically accomplished by mounting the ring 10 on a holder such as that shown in U.S. Pat. No. 5,011,481 (Myers et al.), which is removed once the device sutures are in place. Such holders, however, do not prevent the ring 10 from bunching or pleating when the device sutures are tied off, if the sutures are not precisely placed.

In accordance with the present invention, the need for a holder is obviated (although one could be used if desired) by providing an annuloplasty device (e.g., ring or band) that is generally rigid during implantation and valve testing, but then will soften and become more flexible after the surgical procedure to allow the valve annulus to change geometry with the cardiac cycle. Thus, the present invention provides an annuloplasty device for implantation comprising a band-shaped member having an initial modulus of elasticity as measured by dynamic mechanical analysis (1 Hz, bending, 25° C.) of about 145 kpsi (1 GPa) or more. After implantation in a biological environment, an annuloplasty device of the present invention has a modulus of elasticity of about 14,500 psi (100 MPa) or less.

As used herein, the term "biological environment" typically refers to the body of a patient, particularly, a mammalian patient, and more particularly, a human patient. However, the term "biological environment" can also include an in vitro environment that models a desired in vivo environment, e.g., a temperature of about 37° C. and saline or Ringer's solution.

Significantly, the devices of the present invention maintain their initial modulus of elasticity, which is generally rigid, from manufacture throughout the surgical procedure and testing before the closure of the patient's chest. They have appropriate mechanical strength to prevent breakage due to normal handling both before and during implantation, yet become more flexible within a relatively short period after implantation. They typically become more flexible within a period of no less than about one hour after implantation (or immersion in a biological environment). Preferably, they become more flexible and reach the final modulus of elasticity in no more than about 7 days, and more preferably, in no more than about 3 days after implantation (or immersion in a biological environment).

Devices of the present invention typically, and preferably, include two or more components, at least one of which is a structural component and at least one of which is a flexibilizing component. The structural component provides a means by which the device can be sutured into place in the body of a patient. The flexibilizing component provides a means by which the device can become more compliant (e.g., flexible or soft) after immersion in a biological environment (e.g., implantation). There may also be one or more components that can control the rate the device becomes compliant after implantation. In alternative embodiments, the flexibilizing component and the structural component can be the same, such that the device includes only one material capable of changing modulus once immersed in a biological environment (e.g., inside a patient's body).

In certain embodiments, devices of the present invention include an inner core that includes the flexibilizing component surrounded by an outer sheath that includes the structural component. The structural component can be a biocompatible material that is primarily used for suturing the device into the body of a patient, and is chosen such that it allows for tissue in-growth after implantation. The flexibilizing component can be a high modulus material, such as poly(vinyl alcohol-co-vinyl acetate) (PVA) or poly(vinyl pyrrolidone) (PVP) in the form of a tube or rod, for example, that dissolves once in contact with bodily fluids. The core can also include a third component, such as a silicone perforated sheath around the PVA of PVP, that controls the rate of dissolution of the flexibilizing component. This rate controlling component, which can supplement or be a part of the structural component, may also contain radio-opaque salts for imaging.

Alternatively, devices of the present invention include a structural component that is impregnated with a flexibilizing component. For example, the structural component can include a biocompatible material in the form of a sewn, knitted, braided, or woven tube, rod, or rope, or the like, that is impregnated with a flexibilizing component, such as a polysaccharide, that dissolves or degrades once in contact with bodily fluids. In this way, there is no discrete inner core and outer sheath.

As an alternative, a conventional Duran Ring, as shown in FIG. 1, can be coated over the entire surface of the ring or over a portion of the surface with a flexibilizing component that causes the Duran Ring to be rigid and then dissolves or degrades once in contact with bodily fluids. Also, the soft core of a conventional Duran Ring can be coated or be replaced by, or supplemented with, a flexibilizing component.

In yet another embodiment, a device of the present invention can include a material that undergoes a phase transition after implantation. For example, materials such as Mitsubishi MM-3520 polyurethane are glassy or rigid at 5–20° C. and flexible or soft at 37° C. Alternatively, a device of the present invention can include a material that can be plasticized with water, such as a crosslinked polymer hydrogel, that softens as it absorbs bodily fluids. For example, materials such as poly(2-hydroxyethyl methacrylate) and polyacrylamide are rigid and upon absorbing water become hydrogels, which are more compliant.

The flexibilizing (i.e., softening) mechanism used in designing the devices of the present invention can be controlled by the choice of materials. A wide variety of materials can be used as the flexibilizing component. They are typically chosen such that they do not produce materials that are toxic or detrimental to the body upon softening or dissolving. Similarly, a wide variety of materials can be used as the structural component. They are chosen such that they are biocompatible as defined in ISO 10993-1 (Biological Evaluation of Medical Devices, Part 1: Guidance on selection of tests), allow for suturing to hold a device in place, and allow for tissue in-growth after implantation. Similarly, any other components used in devices of the present invention are chosen such that they are not detrimental to the patient. All components are chosen such that the devices retain sufficient strength to serve their intended purpose for a significant period of time, preferably, for the life of the patient.

Devices of the present invention include one or more materials that incorporate one or more of the following flexibilizing mechanisms: dissolution; biodegradation; plasticization; and phase transition. For dissolution, typically a device softens as a water soluble component, which provides the rigidity when dry, dissolves away. Control of how fast the material loses its rigidity depends upon solubility and diffusion considerations. Many substances can be considered for the water-soluble component, including organic, inorganic, and polymeric materials. Examples include simple sugars such as D-glucose and sucrose, polysaccharides such as a starch guar gum and dextran, and synthetic polymers such as poly(vinyl alcohol-co-vinyl acetate), poly(vinyl pyrrolidone), poly(ethylene glycol), poly(propylene glycol), poly(N-vinyl pyrrolidone-co-vinyl acetate), polystyrene sulfonate, and pharmaceutical-grade derivatized celluloses such as 2-hydroxyethyl carboxymethyl cellulose, carboxymethyl cellulose, ethyl cellulose, methyl cellulose, 2-hydroxy ethyl cellulose, or mixtures thereof. Of these, the poly(vinyl alcohol-co-vinyl acetate) (PVA) and poly(vinyl pyrrolidone) (PVP) are used as core structures, and the saccharides and polysaccharides, as well as PVP and PVA, are used as coatings. Suitable PVA's include those having a molecular weight of about 3,000 to about 200,000 and a percentage hydrolyzed of about 70% to about 100%. Preferred PVA's include those having a molecular weight (weight average) of about 15,000 to about 80,000 and a weight percentage hydrolyzed of about 85% to about 90%. Suitable PVP's include those having a molecular weight of about 20,000 to about 5,000,000. Preferred PVP's include those having a molecular weight of about 500,000 to about 1,500,000.

Biodegradation typically involves the hydrolysis of water-insoluble polymeric materials to water-soluble components by either chemical or biochemical means. Examples of synthetic biodegradable (i.e., bioerodible) polymers include polylactide, polylactide-co-glycolide, polyglycolide, polyglycolide-co-trimethylene carbonate, polycarprolactone, poly(ortho ester), polydioxanone, polyanhydride, poly(hydroxy butyrate), and poly(hydroxy valerate).

Another approach to transforming a device between a rigid and soft device is to plasticize the structural material by absorbing molecules from the surrounding biological environment, such as water. Water, for example, from the implantation environment diffuses into the core to soften the plasticizing material without the material being removed by dissolution or degradation. Again, solubility and diffusion play a major role in determining the rate of softening. An example of such a material is a hydrogel that is rigid when dry and softens by swelling to form a hydrogel. Hydrogel examples include crosslinked polymers poly(2-hydroxyethyl methacrylate) and other hydroxyalkyl methacrylate and acrylates, PVA, PVP, PEO, polyalginate, polyacrylamide, poly(N-alkyl acrylamide), polystyrene sulfonate, and copolymers thereof, and gelatine.

Unlike the mechanisms that rely on water solubility and diffusion, a phase transition mechanism capitalizes on the thermal properties of a material. If the glass transition temperature of the polymer is selected to be between body temperature (about 37° C.) and implantation and/or room temperatures (e.g., about 5–21° C.), or about 30° C., for example, then the material will be rigid during implantation but will soften and turn rubbery as the device site warms back to the homeostatic body temperature after implantation.

Devices of the present invention can be designed to incorporate one or more of the softening mechanisms described above. For example, devices can include a solid rod core design made from a polymer that would provide rigidity when dry. Such a solid rod core could be manufactured by casting, injection molding, or extrusion techniques, for example.

Devices can also include a hollow sheath core design (e.g., a tube) that has the desired flexibility of the implanted device, yet can be filled with a substance that provides stiffness prior to implantation. If this substance softens by dissolving into water, or by being plasticized by water, then holes can be provided in the sheath wall for water penetration/dissolution. An advantage of this design is that the size and number of holes in the sheath provides some control over the softening rate if dissolution, biodegradation, or plasticization are mechanisms of softening. One advantage of this design is that the device can be made radio-opaque for visualization after implantation. This can be done by making the tube which controls the dissolution rate out of, or loading the tube with, a radio-opaque material such as barium sulfate.

An additional design of a device of the present invention includes a single homogenous element that has all the required properties of the implanted device. Such an element might look much like a braid of interwoven fibers in the form of a ring. This structure would be made rigid by selecting a material (a stiffening agent that would function as the flexibilizing component) to coat the braid such that, when dry, would be rigid, and, when wet, would soften by any of the mechanisms described above. For example, the rope could be soaked in various solutions or materials, then the agent dried or cured in place to make the ring stiff. The same three softening mechanisms disclosed above could be used to soften the ring to its final desired flexibility. A braid would allow structural integrity to be maintained if the surgeon inadvertently sutured through the core and broke a strand of the braid.

The devices of the present invention can also be made to release pharmaceutically active agents (e.g., for wound healing) during the softening phase. Examples of pharmaceutically active agents include dexamethazone. They could be incorporated by compounding with the polymer to be softened by solvent coating or traditional melt processes.

Figure 4:
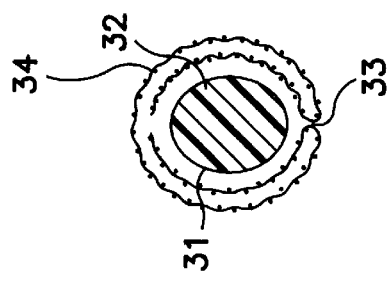
FIG. 4 is a section along line 4—4 of FIG. 2.
Figure 3:
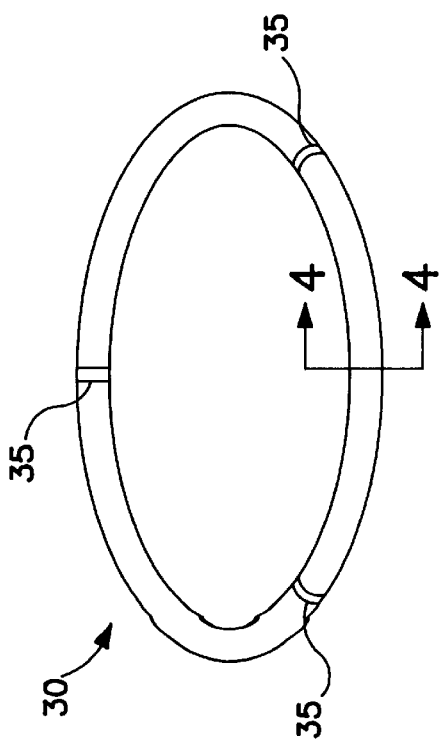
FIG. 3 is a perspective view of one embodiment of an annuloplasty device in accordance with the present invention.

FIGS. 3–4 illustrate a preferred annuloplasty device of the present invention that incorporates one or more of the softening mechanisms and designs described above. FIGS. 3 and 4 show an annuloplasty ring 30 that has a lumen 31 containing a generally rigid rod-like inner core 32 of PVA or PVP, for example. The core 32 is completely enclosed by a sheath 34 of biocompatible cloth made of polyethylene terephthalate, for example. The sheath 34 is made by folding a cloth sheet around the core 32 and sewing the folded ends together at 33, as is done for a conventional Duran Ring. The combination of the core 32 and sheath 34 result in a ring which is completely rigid. After it is implanted, the PVA or PVP dissolve in bodily fluids leaving the sheath 34, which is flexible yet essentially minimally extensible. The ring 30 has three trigone markers 35 sewn thereon at intervals to assist the surgeon in the placement of sutures. Although this device is in the form of a circular closed ring, it can also be in the form of a D-shaped ring, or an open ring such as a C-shaped ring, for example.

Figure 5:
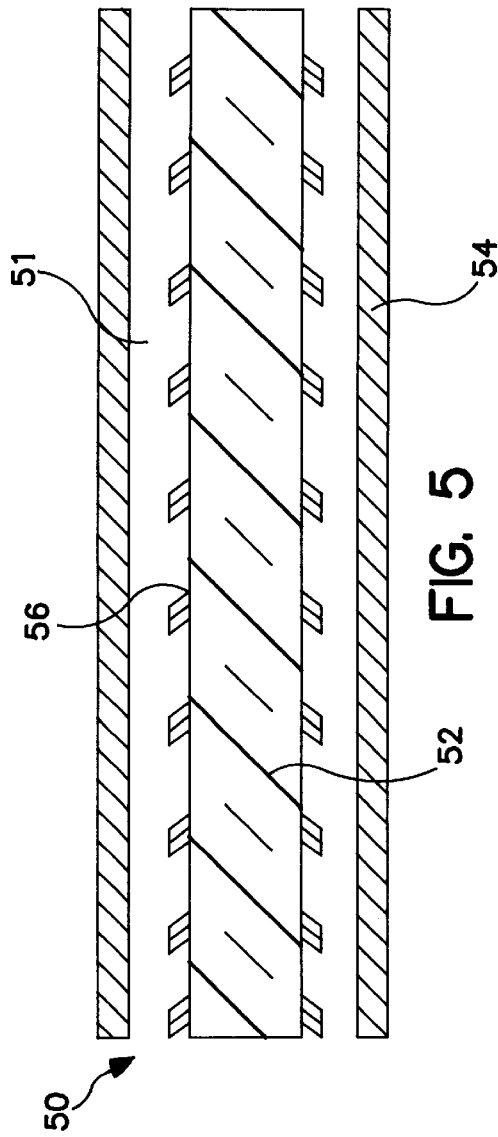
FIG. 5 is a cross-sectional view of an alternative embodiment of an annuloplasty device in accordance with the present invention.

FIG. 5 illustrates an alternative preferred annuloplasty device of the present invention that incorporates one or more of the softening mechanisms and designs described above. FIG. 5 shows a cross-sectional view of an annuloplasty ring 50 that has a lumen 51 containing a generally rigid rod-like inner core 52 of PVA or PVP, for example. The core 52 is completely enclosed by an outer sheath 54 of biocompatible cloth made of polyethylene terephthalate, for example. Between the core 52 and the outer sheath 54 is a perforated inner sheath 56. This can be made of silicone, for example. This perforated sheath does not dissolve, yet is flexible, and because of the perforations, it controls the rate of dissolution of the inner core material (e.g., PVA or PVP). It can provide additional structural support to the device; however, its main function is to control the rate of dissolution of the inner core material. The combination of the core 52, the outer sheath 54, and the perforated inner sheath 56, result in a ring which is completely rigid. After it is implanted, the PVA or PVP dissolve in bodily fluids leaving the outer sheath 54 and the inner sheath 56 intact, which are flexible yet essentially minimally extensible.

EXAMPLES

Example 1

Five coated Dacron polyester fabric swatches were prepared using the formulations listed in Table 1. Samples #1 and #2 were dissolved in water at concentrations of 20% and 15% total solids, respectively. Samples #3–5 were dissolved in boiling water at a concentration of 5%. These samples were prepared by dip coating the fabric 3 times in aqueous solutions of the polymers, with air drying overnight in between. Testing for softening was at 37° C. in Ringer's solution.

TABLE 2

Formulations for annuloplasty ring softening mechanism experiments

| Sample # | Formulation |
| --- | --- |
| 1 | 50% PVP MW 1,000,000/50% PVA MW 108,000, 99.7% hydrolyzed |
| 2 | 67% PVA MW 108,000, 99.7% hydrolyzed/33% dextran MW 3,000,000 |
| 3 | PVA MW 108,000, 99.7% hydrolyzed |
| 4 | PVA MW 78,000, 98% hydrolyzed |
| 5 | PVA MW 133,000, 99% hydrolyzed |

The softening rate results are listed in Table 3. The score for the relative stiffness (0=soft, 1=slightly stiff, 2=stiff, 3=very stiff, 4=hard, and 5=very hard) was based on how they felt upon being flexed by hand. The control was an uncoated sample and was assigned a score of 0. The formulations were appropriately hard or stiff at the start of the test (when dry). Between 22 minutes and 52 minutes in the Ringer's solution, each of the samples softened considerably from stiff to slightly stiff. It was thought that this transition was due to the polymer swelling with the Ringer's solution, forming a thin gel layer. The hardness then did not greatly decrease between 52 minutes and 53 hours of test time.

TABLE 3

Softening rate data for the five coated fabric formulations at 37° C. in Ringer's solution (min = minutes, hrs = hours)

| Sample # | 0 min | 22 min | 52 min | 5 hrs | 5.5 hrs | 28.5 hrs | 53 hrs | Dried |
|---|---|---|---|---|---|---|---|---|
| 1 | 4 | 2 | 1 | 1 | 1 | 1 | 1 | 4 |
| 2 | 4 | 2 | 1 | 1 | 1 | 1 | 1 | 4 |
| 3 | 3 | 2 | 1 | 1 | 1 | 1 | 1 | 2 |
| 4 | 3 | 2 | 1 | 1 | 1 | 1 | 1 | 2 |
| 5 | 3 | 2 | 1 | 1 | 1 | 1 | 1 | 2 |

Sample 1 containing the PVP had a slippery feel to the surface that may not be desirable for handling when wet. When the samples were dried after the test at 40° C. overnight, they appeared to be similar in stiffness to the sample prior to testing in Ringers solution. This suggested that the hydrated polymer gels were not appreciably dissolving over the 53 hours test time.

The same samples were tested in the same softening experiment, but at 10° C. (in a refrigerator). This was done to see if there was any gross difference in softening rate due to the temperature. Since it was understood that the surgical area is cooled after the heart is stopped, a lower temperature could affect the softening rate of these polymers. Table 4 shows that the results were very similar to the data at 37° C. in Table 3. There was no measurable difference due to temperature.

TABLE 4

Softening rate data for the five coated fabric formulations at 10° C. in Ringer's solution

| Sample # | 0 min | 22 min | 52 min | 1.2 hrs | 2.2 hrs | 20 hrs | Dried |
|---|---|---|---|---|---|---|---|
| 1 | 4 | 2 | 1 | 1 | 1 | 1 | 4 |
| 2 | 4 | 2 | 1 | 1 | 1 | 1 | 4 |
| 3 | 3 | 2 | 1 | 1 | 1 | 1 | 2 |
| 4 | 3 | 2 | 1 | 1 | 1 | 1 | 2 |
| 5 | 3 | 2 | 1 | 1 | 1 | 1 | 2 |

This experiment indicates that hard coatings did transition to softer ones, demonstrating feasibility of the dissolution softening concept. The PVA, PVP, and dextran materials did not show a great temperature dependence. These samples did not remain hard for 60 minutes.

Example 2

A Duran Ring was dipped into a solution of the dissolved polymer and allowed to air dry, typically overnight. The stiffness was controlled by the number of coatings applied. From the previous fabric coating experiments, it was thought that coating more than 3 times may be necessary to keep the ring sufficiently hard through 60 minutes. Using PVA (99.7% hydrolyzed; 108,000 MW) and dextran (3,000,000 MW), 2.5% solutions were prepared in water. Up to 10 coatings were made on each ring, with drying in air overnight between each coating. One ring was coated first with 7 coats of dextran, then with 3 coats of PVA to make it stiffer (Table 5). The 10-coat PVA ring was very hard; a suturing needle could not be easily passed through it. The 10-coat dextran ring was only slightly stiff, and could be penetrated relatively easily with the needle.

TABLE 5

Duran Rings coated on the fabric.

| Sample # | Coating solution[a] | Number of coats | Stiffness |
|---|---|---|---|
| 1 | 2.5% PVA | 7 | Very hard |
| 2 | 2.5% PVA | 10 | Very hard |
| 3 | 2.5% dextran | 7 | Slightly stiff |
| 4 | 2.5% dextran | 10 | Slightly stiff |
| 5 | 2.5% dextran, then 2.5% PVA | 7, then 3 | Very stiff |

[a]- PVA 108,000 MW, 99.7% hydrolyzed; dextran 3,000,000 MW

Four of these ring samples were tested for stiffness as described above after soaking in saline at 37° C. The score for the relative stiffness (0=very hard, 1=very stiff, 2=stiff, 3=slightly stiff, 4=flexible) was based on how they felt upon being flexed by hand (note this scale is opposite to that used in Example 1). Table 6 shows these results. The 7-coated dextran rings were not that stiff to start, and they softened very quickly. Apparently, the dextran dissolved very rapidly. The ring with seven dextran coats, then three PVA coats was only marginally slower to lose stiffness. However, the 10- and 7-coated PVA rings were very hard initially, and remained stiff for much longer. The 7-coated PVA remained stiff for 5 hours, while the 10 coated PVA was still stiff after 18 days. Apparently, this PVA (99.7% hydrolyzed, 108,000 MW) was very slow to dissolve. The rings did not return to the same suppleness as the control Duran Ring within 18 days.

TABLE 6

Softening[a] stiffness loss data for the coated rings of Table 5.

Stiffness Scale (0 = stiff to 4 = flexible)

| Time | Dextran 7 coats | Dextran 7/ PVA 3 coats | PVA 7 coats | PVA 10 coats | Control |
|---|---|---|---|---|---|
| Initial | 3 | 1 | 0 | 0 | 4 |
| 15 min | 4 | 3 | 2 | 1 | 4 |
| 30 min | 4 | 3 | 2 | 1 | 4 |
| 45 min | 4 | 4 | 2 | 2 | 4 |
| 1 hr | 4 | 4 | 2 | 2 | 4 |
| 1.5 hr | 4 | 4 | 2 | 2 | 4 |
| 2 hr | 4 | 4 | 2 | 2 | 4 |
| 5 hr | 4 | 4 | 2 | 2 | 4 |
| 7 hr | 4 | 4 | 3 | 2 | 4 |
| 8 hr | 4 | 4 | 3 | 2 | 4 |
| 9 hr | 4 | 4 | 3 | 2 | 4 |
| 24 hr | 4 | 4 | 3 | 2 | 4 |
| 2 days | 4 | 4 | 3 | 2 | 4 |
| 4 days | 4 | 4 | 3 | 2 | 4 |
| 18 days | 4 | 4 | 3 | 2 | 4 |

[a]- 37° C. in saline; n = 1

Table 7 shows weight change of the samples of Table 5. Although the control (not coated) ring was not weighed, it appears that the three rings containing PVA gained about 5 to 6% in weight through 18 days. The dextran ring (7 coats) gained about 14% during the same time.

TABLE 7

Softening[a] weight change data for the coated rings of Table 5.

| | Ring weight (gm) | | | |
|---|---|---|---|---|
| Time | Dextran 7 coats | Dextran 7/ PVA 3 coats | PVA 7 coats | PVA 10 coats |
| 15 min | 1.3 | 1.4 | 1.2 | 1.4 |
| 30 min | 1.3 | 1.4 | 1.2 | 1.4 |
| 45 min | 1.4 | 1.4 | 1.2 | 1.4 |
| 1 hr | 1.4 | 1.4 | 1.8 | 1.4 |
| 1.5 hr | 1.35 | 1.44 | 1.18 | 1.44 |
| 2 hr | 1.41 | 1.48 | 1.21 | 1.44 |
| 5 hr | 1.40 | 1.40 | 1.21 | 1.44 |
| 7 hr | 1.33 | 1.39 | 1.20 | 1.45 |
| 8 hr | 1.34 | 1.38 | 1.21 | 1.46 |
| 9 hr | 1.35 | 1.35 | 1.20 | 1.47 |
| 24 hr | 1.43 | 1.49 | 1.23 | 1.50 |
| 2 days | 1.39 | 1.39 | 1.20 | 1.50 |
| 4 days | 1.40 | 1.40 | 1.27 | 1.51 |
| 18 days | 1.48 | 1.48 | 1.26 | 1.49 |

[a]- 37° C. in saline

These rings were dip-coated in PVA and were too rigid; a suturing needle could not be passed through them. Since it was not possible to maintain a reasonable softening rate with a coating much less stiff, it was decided to coat only the inside circumference of an annuloplasty ring. The sutures are typically placed on the outer-under side of the ring, i.e., at about 7:30 and 4:30 in a cross-sectional view. In addition, due to the long time that the previous set of rings took to dissolve the PVA, an attempt was made to make these rings less rigid.

The inner circumference of the fabric of a Duran Ring was painted with a 5% solution of the 133,000 MW 99% hydrolyzed PVA using a small brush. Two coats were applied, followed by air drying overnight. Subsequent coatings were applied with a few hours drying in between. Table 8 shows the composition of the samples made. Evan's Blue dye (used intravenously to determine blood volume) was used to demonstrate how the solution wicked away from the target area as it was painted. The dye was dissolved in the PVA solution at a concentration of 0.03%. The dye helped to demonstrate just where the PVA was placed on the inner circumference. The ring's outer (uncoated) edge was soft while the coated part was hard. The samples were coated with a 10% PVA solution that was applied while the ring was on its oval-shaped Delrin holder. In this way, the proper shape of the ring was maintained.

TABLE 8

Duran rings coated on the inner diameter with PVA (133,000 MW, 99% hydrolyzed)

| Sample # | Coating solution[a] | Number of coats | Weight gain, % |
|---|---|---|---|
| 1a | 5% PVA | 3 | 1 |
| 1b | 5% PVA/dye | 3 | 1 |
| 2a | 5% PVA | 6 | 5 |
| 2b | 5% PVA/dye | 6 | 5 |
| 3a | 5% PVA | 10 | 8 |
| 3b | 5% PVA/dye | 10 | 8 |
| 4a | 10% PVA | 3 | 2 |
| 4b | 10% PVA/dye | 3 | 2 |
| 4c | 10% PVA/dye | 3 | 2 |

[a]- The dye was Evan's Blue

The rings were made quite stiff and softened within about 2 to 3 hours. The inner circumference coating with PVA did not make the ring stiff enough, overall. In addition, it was difficult to suture through since some surgeons will want to place sutures directly through the ring (i.e., at the 12:00 and 6:00 positions), and PVA coating in that area prevents that. However, it is believed that a partially coated ring could be made viable.

A study was undertaken to determine the effect of molecular weight and percentage hydrolysis of the PVA on its rate of dissolution. PET fabric swatches were dip coated twice in 10% solutions of PVA of different MW or percentage hydrolysis and dried (Table 9). All PVA solutions contained Evan's Blue dye to visually determine if PVA remains on the fabric after soaking. All coated samples were stiff, compared to an uncoated control. Samples were placed in water at room temperature; within 3 minutes all samples lost most of their torsional stiffness (by hand). After 2 hours, the samples were removed from the water and dried.

TABLE 9

Effect of MW and percentage hydrolysis on the softening rate of PVA

| Sample # | PVA MW | PVA % Hydrolyzed | Results after 2 hours in 25° C. water |
|---|---|---|---|
| 1 | 78,000 | 98 | Hard; slight blue tint |
| 2 | 78,000 | 88 | Soft; no blue |
| 3 | 25,000 | 98 | Stiff; blue |
| 4 | 25,000 | 88 | Soft; no blue (like uncoated control) |
| 5 | 125,000 | 88 | Slightly stiff; no blue |

The results of Table 9 indicate that the percentage hydrolysis is more important than the molecular weight for completely dissolving the PVA. Higher molecular weight did have the expected effect of slowing the PVA dissolution, but its effect was not nearly as great as the percentage hydrolysis. The 98% hydrolyzed samples (samples 1 and 3) still retained PVA after 2 hours in solution; they were stiff and blue colored. However, the 88% hydrolyzed PVA samples (samples 2, 4, and 5) had lost much, if not all, of their stiffness in this same time. The reason for this is the crystallinity of the PVA. It is well known that the higher percentage hydrolyzed samples have higher crystallinity. When PVA is manufactured, it is first made as poly(vinyl acetate), PVAc. The acetate groups are hydrolyzed to give the alcohol, making poly(vinyl alcohol), PVA, as shown below. The greater the hydrolysis, the less acetate groups are left and the more hydroxyl groups are produced. PVA is much more crystalline than PVAc, due to the high concentration of hydroxyl groups which can lead to hydrogen bonding. In general, highly crystalline materials will dissolve more slowly. Using 88% hydrolyzed PVA will allow complete dissolution in a reasonable time period.

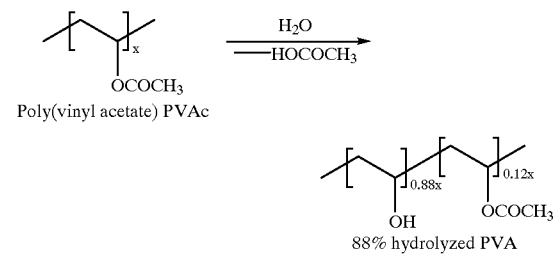

This example demonstrates that coating the ring fabric with 88% hydrolyzed PVA produced samples that remained stiff for no more than 2 hours, but they did demonstrate the softening concept.

Example 3

Annuloplasty rings were made having rigid but water-soluble rods inside the fabric. PVA rods (88% hydrolyzed, 25,000 MW) were extruded at 200° C. using the Tinius Olsen Melt Index apparatus. After two minutes of preheat, 20 Kg force was used to extrude the melt. From a DSC experiment (10° C./min.), the 88% hydrolyzed 25,000 MW PVA had a Tg of 54° C. and a Tm of 177° C. A 27-mm Duran Ring was cut in half along its sutures, the silicone core was slid out, and a 2.0 mm diameter×85 mm long PVA rod was slid in this fabric tube. After heating in an oven at 85° C. for a few minutes to soften the PVA, the fabric/rod length was shaped easily around the Delrin holder for the 27 mm ring. The ring ends were subsequently sewn together. The ring was very hard and rigid where the rod was present, but more flexible where the rod ends (unjoined) came together.

TABLE 10

Softening rate experiment of the first PVA 2.0 mm diameter rod-in-ring prototype.

| Time in water | Stiffness | Comments |
|---|---|---|
| Initial | Hard, rigid | Ring floats on water |
| 12 minutes | Rigid | Ring sinks under water; no swelling and not slippery |
| 30 minutes | Rigid | Slight swelling; not slippery |
| 1 hour | Slightly less rigid | Slightly more swelling; not slippery |
| 2 hours | Much more flexible, retains molded shape | Not slippery; stiffer than the control ring |
| 3 hours | As flexible as control | Soft PVA gel still inside ring; not slippery |
| 4 hours | As flexible as control | Soft PVA gel still inside ring; not slippery |
| 22 hours | As flexible as control | PVA all dissolved |

This sample was tested for softening rate in a 25° C. water bath with continuous flow. The prototype was removed and evaluated by hand for stiffness and subjective feel during the test. An unmodified Duran Ring was used as a control. Table 10 shows that the ring remained rigid for at least 1 hour, losing most of its rigidity between 1 and 2 hours. After 3 hours, it became as flexible as a control Duran Ring. PVA gel was noted in the ring between 3 and 4 hours. Through 4 hours, the ring was not slippery to the touch and it swelled only very slightly. After about 22 hours, the ring was removed and cut open. No PVA was observed; it was totally dissolved. Additional rings were prepared for further evaluation. The same 88% hydrolyzed, 25,000 MW extruded PVA rods were used, but with smaller diameter (1.2–1.3 mm). The 2.0 mm diameter rods seemed to be too bulky for the fabric as sewn. The dry modulus of this rod was measured by DMA (1 Hz, bending at 25° C.) to be 13.2 GPa, comparing favorably with titanium (the core of the Carpentier ring) at about 103 GPa. Another sample ring was prepared as described above, except the silicone insert with a radio-opaque marker was assembled along side of the PVA rod in the fabric to see if it handled any differently. Although both had the same stiffness and softened at the same rate (reached a "leathery" modulus of about 50 MPa in about 1 hour by DMA testing), the ring with the silicone insert felt somewhat "cushier". This sample was tested in an isolated pig heart. No buckling was observed. When the heart was placed in 37° C. saline, the ring became flexible in about 20 minutes. The PVA rod ends, being unjoined, added more flexibility to the ring than if they were somehow fused.

Extrusion of PVA is difficult since degradation and crosslinking of the melt can occur. Since lower molecular weight PVA typically extrudes easier, rods were extruded at 220° C. in the melt indexer using 88% hydrolyzed PVA of molecular weights 25,000, 10,000, and 3,000. Each rod sample was about 1 inch in length, had a diameter of 1.9–2.1 mm, and weighed about 100 mg. The 3,000 MW rod was more brittle than the others. The rod samples were placed in 25° C. water and checked by hand for stiffness for up to 2 hours. Table 11 shows that the 3,000 MW PVA dissolved much faster than the 10,000 and 25,000 MW PVA. Since the dissolution rate was faster than desired, PVA of MW about 25,000 was more desirable to use.

TABLE 11

Effect of molecular weight on the softening rate of 88% hydrolyzed PVA rods

| Sample # | PVA MW | 1 hour comments | 1.5 hour comments | 2 hour comments |
|---|---|---|---|---|
| 1 | 3,000 | Almost all dissolved, soft | Dissolved | Dissolved |
| 2 | 10,000 | Rigid | Rigid, slimmer | More flexible, firm |
| 3 | 25,000 | Rigid | Rigid, slimmer | More flexible, firm |

If the rod interferes with suturing, then the rod cross sectional geometry or size may be changed. For instance, using a smaller diameter rod, or using a rod of maximal diameter but with a D-shaped cross section, may provide additional room for suturing.

This example demonstrates that extruded PVA (88% hydrolyzed, 25,000 MW) could be formed into rods that have very acceptable stiffness. These rods will soften between 1 and 2 hours, eventually completely dissolving.

Example 4

This example provides a ring containing a PVA rod with a radio-opaque filler and rod ends joined. A PVA rod made from AIRVOL 205 PVA (87–89% hydrolyzed, 40,000–60,000 MW) available from Air Products and Chemicals, Inc. (Allentown, Pa.) was extruded in a single screw extruder (185° C. melt temperature, 210° C. die temperature, TRPM screw). The PVA rod was placed inside a silicone tubing. The tubing was swollen with hexane so that the tubing could be slipped over the ends of the rod (joined or not). When the hexane evaporated from the silicone the tubing shrunk tightly over the rod. The ID of the silicone tubing was about half the OD of the PVA rod. Pairs of small holes were punched through the silicone tubing (2 holes on opposite sides of the tubing) to allow water penetration for the PVA dissolution. The size and frequency of the hole pairs were proposed to control the softening rate. Typically, the hole pairs were placed slightly less than 1 cm apart from each other along the tubing length. The holes were punched through the tubes with two sizes of disposable cannula, creating holes of about 0.5 mm or 0.9 mm diameter. The smaller (0.5 mm) holes were less prone to splitting when the tubing was swelled in hexane. The holes were about every 1.3 cm (0.77 holes/cm).

The softening rate of a PVA rod in the silicone sheath was measured in water by DMA. Using a bending mode, the Perkin Elmer DMA-7e dynamic mechanical analyzer was used to monitor the complex modulus of the sample as it softened in 25° C. water. The 15 mm dual cantilever measuring system was used. A small static force (2 mN) was used after mounting the sample, and the dynamic force was 400 mN at 0.1 Hz. The dynamic force was varied throughout the run to maintain a 10 μm amplitude. The static force was varied throughout the run to maintain the average position of the probe with no deflection. At the start of a run, the DMA would be started just before immersing the DMA/PVA rod assembly into the 25° C. water, since there always was a very early (within the first 2 minutes) loss in the modulus after becoming wet. DMA softening rate tests showed that a straight PVA rod covered with this perforated silicone tube drastically increased the softening time. Decreasing rod diameter or increasing the sheath hole density shortened the softening time.

The open ends of the tube were sealed with silicone adhesive. To estimate softening time, the DMA log modulus (complex) was extrapolated to 20 MPa. The log modulus appeared to be linear with time only after a lag time. This induction time appeared to decrease with increasing hole density and decreasing rod diameter. The softening time of the PVA rod was extended by varying the rod diameter and sheath perforation density. The softening time for a 1.4 mm diameter AIRVOL 205 PVA rod without the silicone sheath was about 1.25 hours. The softening time for a 1.4 mm diameter rod increased to about 6.5 hours when the silicone sheath was perforated to 0.93 holes/cm, and it increased further yet to about 8.5 hours when the perforation density decreased to 0.80 holes/cm. The effect of rod diameter was demonstrated with the 0.80 holes/cm sheaths; the softening time of the 1.4 mm diameter rod decreased from about 8.5 hours to about 5 hours for the 1.07 mm diameter rod. In all cases, the PVA eventually dissolved completely and diffused out of the perforated silicone sheath. The tubing for sample with the 1.07 mm diameter rod was loaded with barium sulfate for a radio-opaque marker.

Although the silicone sheath can keep unjoined rod ends rigid, the ends of the sample devices were rabbeted and fused by gluing with a 10% solution of PVA. Usually several coats were applied to make a strong bond. The silicone tube was cut long so that the extra length could be pulled over the joint. It was determined that the ring manufactured easier if there was no holes perforated in this extra length that covered the rod ends.

Two of these samples were made with AIRVOL 205 extruded PVA rods and were evaluated. Sample 1 contained a 1.4 mm rod with 0.9 mm diameter holes punched at a density of 1.21 holes/cm. Sample 2 contained a 1.8 mm rod with 0.5 mm diameter holes punched at a density of 1.43 holes/cm. Smaller holes had to be used with the 1.8 mm rod because the large holes caused the tube to rip when the rod was being inserted. It was thought that the 1.4 mm rod was sufficiently rigid for this application due primarily to the joining of the PVA ends with the glue and the sheath. The 1.8 mm rod was included since its rigidity more closely matched the feel of a Carpentier titanium core ring. However, the overall diameter of the 1.8 mm rod inside the sheath and sewing fabric was felt to be quite wider than a typical Duran Ring.

Table 12 shows the results of the evaluation. The rings were sewn in an isolated pig heart in either the mitral position (1.4 mm; sample 1) or the tricuspid position (1.8 mm; sample 2). The heart was submerged in a continuously flowing 37° C. saline bath.

TABLE 12

Evaluation of the softening rate characteristics of the rod-in-silicone sheath prototype in excised pig hearts

| Hours | Score for 1.4 mm rod, 0.9 mm holes @ 1.21 holes/cm | Score for 1.8 mm rod, 0.5 mm holes @ 1.43 holes/cm |
|---|---|---|
| Initial | 0 | 0 |
| 0.25 | 0 | 0 |
| 0.5 | 0 | 0 |
| 0.75 | 1 | 0 |
| 1 | 2 | 0 |
| 1.25 | 2 | 0 |
| 2 | 3 | 0 |
| 2.25 | 3 | 0 |
| 2.5 | 3.5 | 0 |
| 3 | 4 | 0 |
| 14 | 4 | 2.5 |

Score = 0 (very hard) to 4 (soft)

The data suggests that over 3 hours the 1.8 mm device stayed rigid, while the 1.4 mm ring lost most of its rigidity by about 2.5 hours. The 1.8 mm rod was expected to soften slower since it is a thicker sample and the holes were significantly smaller. It still had some rigidity even after 14 hours. When comparing the 1.4 mm diameter sample in this test to the 1.4 mm rods in the DMA softening experiment described above, the effect of hole density was confirmed. A softening time of sample 1 was calculated to be 2.2 hours based on a linear extrapolation of softening time as a function of hole density. The actual softening time here was very close to this 2.2 hour estimation, between 2.5 and 3 hours, suggesting that the DMA softening test correlates well to softening in this excised heart model.

Using this DMA softening test, the log complex modulus was fairly linear with time. For this 1.4 mm AIRVOL 205 extruded rod, the extrapolated time to softening to 20 MPa was estimated at 78 minutes.

The weight loss of PVA rods was determined as follows. PVA rods (AIRVOL 205 rods, 1.4 mm diameter, 1 inch long) were first dried in a 60° C. vacuum oven for 48 hours. Each rod was weighed separately. One rod was placed in a container and 50±2 ml of deionized water was added at 21° C.; it was shaken gently as the rod dissolved. Enough containers were prepared to be able to remove one rod periodically to measure its dry remaining weight. Sampling consisted of removing the rod from the container, padding dry carefully while in a plastic weigh boat, and drying at 60° C. in a vacuum oven overnight. The weight loss was calculated as the difference between the initial dry weight and the remaining dry weight. Two runs were done on the same lot of rods, one with 30 minute sampling intervals and the other with a more appropriate 15 minute sampling intervals. The data in Table 13 show that the rods were completely dissolved within about two hours, agreeing well with the more gross dissolution test data in Table 11. The dissolution profile was fairly linear with time; the average (composite) rate of weight loss through the first 60 minutes was 0.92%/minute (% wt loss=2.6+0.92 minutes). At one hour, 58% of the rod had dissolved.

TABLE 13

Dissolution of AIRVOL 205 rods (1.4 mm diameter, 1 inch long) in 21° C. deionized water

| Sample # | Initial wt, gm | Minutes | Weight sampled, gm | % Weight lost | Comments |
|---|---|---|---|---|---|
| 1 | 0.049 | 30 | 0.032 | 35 | Slightly swelled |
| 2 | 0.046 | 62 | 0.020 | 57 | Soft, difficult to pick up |
| 3 | 0.056 | 91 | 0.009 | 84 | Not much left |
| 4 | 0.043 | 120 | 0 | 100 | Gone |
| 5 | 0.045 | 15 | 0.036 | 20 | |
| 6 | 0.056 | 30 | 0.039 | 30 | |
| 7 | 0.055 | 46 | 0.030 | 45 | |
| 8 | 0.049 | 60 | 0.021 | 57 | |
| 9 | 0.045 | 75 | 0.003 | 93 | Mush, hard to pick up sample |
| 10 | 0.051 | 80 | 0.003 | 94 | Mush |

This example demonstrates that PVA (88% hydrolyzed, 25,000 MW) can be extruded into rods which retain rigidity for more than 60 minutes. The softening of the PVA rod can be modulated by the frequency and size of holes in a silicone sheath. DMA was shown to sure softening characteristics with time, and the method correlated to an ex vivo test.

Example 5

This example was carried out to determine how best to sterilize A rods. Extruded AIRVOL 205 PVA 1.4 and 1.6 mm diameter rods were sterilized by gamma, ethylene oxide (EtO), and gas plasma hydrogen peroxide ($H_2O_2$). The gamma sterilization was performed by isomedix Operations, Libertyville Ill. The rod samples were sterilized either at a normal dose (19.2 kGy) or at a high dose (41.7 kGy). The EtO sterilization was performed by Medtronic Sterilization Services. The procedure was similar to that done on the Duran Ring product (3 cycles, 100% EtO). The peroxide sterilization was performed by Advanced Sterilization Products (Division of Johnson & Johnson Medical, Inc., Irvine, Calif.). Rods were processed through three full STERRAD cycles.

After extrusion the PVA became slightly yellow, but was clear. By visual observation, the extruded rod samples sterilized by the EtO or the gamma looked as they did prior to sterilization; however, the peroxide gas sterilized samples appeared slightly hazy.

Using optical microscopy (160x), the surfaces of rods sterilized by these three methods were compared to unsterilized rods. Visually, the gamma-sterilized rods appeared very similar to the unsterilized rods, although die lines were somewhat more pronounced. The gas plasma peroxide sterilized rod samples showed that there were many small bubbles visible formed on, or just below, the surface. This is what made these samples appear hazy. The extrusion die lines were very similar to the unsterilized controls.

A series of tests were run on the sterilized rods to determine if sterilization affected the AIRVOL 205 PVA in any way. Since any of these sterilization methods are potentially chemically reactive, FTIR analysis of the bulk of the rod was performed. Sterilized and unsterilized rod samples were completely dissolved in water over a 2 hour period at room temperature to a concentration of 1%. The unprocessed, unsterilized control sample was clear, but all of the other extruded samples (sterilized or not) were very slightly hazy, indicating that there may have been some changes in the polymer due to extrusion. Thin films of each of these solutions were cast on glass microscope slides, and analyzed with a Perkin Elmer 1720-X FTIR spectrometer (microscope with attenuated total reflectance objective). When compared to unsterilized extruded rod, there was no difference in the spectra due to gamma or EtO sterilization. The peroxide sterilized rods were not tested by FTIR. When the spectrum of unprocessed and unsterilized PVA resin granules was compared to the spectra of EtO sterilized, gamma sterilized, and two unsterilized PVA rods, a slight decrease in the 1733 $cm^{-1}$ ester carbonyl peak and a subsequent increase in the 1713 $cm^{-1}$ carboxylic acid peak was noted for processed PVA. This seems to have been due to a slight hydrolysis of the remaining 12% (nominal) acetate groups on the Airvol 205 during extrusion. Using a Bio-Rad UMA-500 FTIR, the surface of the extruded rod samples were not found to be different after EtO or gamma sterilization.

To determine if the sterilization procedures degraded the polymer and resulted in a loss in molecular weight, gel permeation chromatography (GPC) was run. The GPC was performed on a Waters 150-CV at 1 ml/min in 0.1M $NaNO_3$ using a refractive index detector. PVA standards (98% hydrolyzed) were used to calibrate, but since the calibration was linear only through the major portion of the eluted curve (not including the leading and receding tails of the curve), only peak molecular weights were reported. Table 14 shows that the PVA did not degrade in molecular weight after extruding. Additionally, the molecular weight did not decrease after EtO or gamma sterilization. However, there possibly was some degradation in the molecular weight noted after peroxide sterilization.

TABLE 14

Molecular weight analysis of PVA resin, rods, and sterilized rods by GPC

| Sample # | Description | Peak Molecular Weight |
|---|---|---|
| 1 | Unprocessed resin | 40,200 ± 2,400 |
| 2 | Unsterilized extruded rod | 43,600 ± 2,400 |
| 3 | Gamma sterilized rod | 40,800 ± 3,900 |
| 4 | EtO sterilized rod | 43,200 ± 6,600 |
| 5 | Peroxide sterilized rod | 32,700 |

The thermal properties of the PVA samples were measured by DSC using a Perkin Elmer DSC-7, scanning under nitrogen at 20° C./minute (first scan data was used). Table 15 shows that although he glass transition temperature (Tg) of the unsterilized rod was unchanged from the unprocessed unsterilized resin, the melting was different. The rod's melting peak temperature (Tm) and the enthalpy (ΔHm) was one peak with a lower enthalpy, indicating lower crystallinity. The PVA resin granules had three distinct melts, while the extruded rod had only one, which was about half the crystallinity. Although the molecular weight had not changed with extrusion, the crystallinity appears to have been lessened.

TABLE 15

DSC data for PVA resin, rods, and sterilized rods

| Sample # | Description | Tg (° C.) | Tm (° C.) | ΔHm (J/gm) |
|---|---|---|---|---|
| 1 | Unprocessed resin | 54 | 145, 163, 190 | 78 |
| 2 | Unsterilized extruded rod | 54 | 177 | 34 |
| 3 | Gamma sterilized rod | 45 | 169, 175 | 55 |
| 4 | EtO sterilized rod | 31 | 170 | 67 |
| 5 | Peroxide sterilized rod | 30 | 170 | 48 |

There were differences noted in the DSC data for sterilized samples. Table 15 shows that the Tgs of the gamma, EtO and peroxide sterilized rods were less than the extruded resin. Since the molecular weights of the EtO and gamma sterilized samples were not different from the unsterilized rod, these results may have been due to plasticization of the samples by moisture. They were not specially dried after sterilization. The EtO and peroxide sterilization does take place in a moist environment, although the end of the sterilization cycle does dry the sample in a vacuum. Their Tgs were less than the Tg of the gamma sterilized rod (31° C. and 30° C. vs. 45° C., respectively). The melting endotherms of the samples were also different (Table 15). The sterilized samples appeared to have been more crystalline (higher ΔHm) than the unsterilized rod. In addition, the peroxide sterilized sample looks like it was quenched from a high temperature, since a crystallization exotherm was noted at about 150° C.

The tensile properties of the rods are given in Table 16. Rods (n=6; 1.4 to 1.6 mm diameter) were pulled at 1 inch/minute on an MTS Sintech 1/D tensile tester at ambient conditions. The two lots of unsterilized rods showed the differences you could expect the PVA to have when the samples are not kept dry. The older rods were stored at ambient conditions (unpackaged) for 8 months prior to testing. The more recently extruded rods were stored in the same way for 4 months prior to testing. Very slowly, water from the atmosphere began to plasticize the rods. As expected, the more recently extruded unsterilized rod had a much higher modulus and lower elongation, and was therefore stronger than the older rods. A comparison of the sterilized rods to the more recently extruded unsterilized rod shows that the EtO, gamma and peroxide sterilized samples lost some modulus and some strength, but were still very hard and strong. Note that the peroxide sterilized samples became much more brittle (very low elongation), leading to a drastic loss in toughness. This may be important to handling the ring. You want the ring to be rigid (high modulus) and strong enough to prevent breaking by typical handling. Toughness is a measure of the energy to break. Clearly, peroxide sterilized samples broke much easier than EtO and gamma sterilized samples.

TABLE 16

Tensile data for PVA rods, sterilized and unsterilized.

| Sample # | Description | Young's modulus (psi) | Tensile strength (psi) | Toughness (in-lb/ cu. in) | Elongation (%) |
|---|---|---|---|---|---|
| 1 | Unsterilized (recent) | 349,000 ± 18,000 | 19,300 ± 600 | 4,740 ± 5,510 | 61.6 ± 75.9 |
| 2 | Unsterilized (older) | 118,000 ± 13,000 | 7,690 ± 810 | 7,830 ± 2,150 | 162 ± 39 |
| 3 | EtO sterilized | 249,000 ± 76,000 | 13,400 ± 1,700 | 2,880 ± 1140 | 46.5 ± 21.9 |
| 4 | Gamma sterilized | 290,000 ± 79,000 | 15,800 ± 1,600 | 3,840 ± 700 | 57.9 ± 12.5 |
| 5 | Peroxide sterilized | 241,000 ± 34,000 | 14,000 ± 800 | 442 ± 118 | 7.9 ± 1.9 |

The DMA softening rate test was performed on these AIRVOL 205 sterilized rods. The ethylene oxide and gamma sterilized rods were very similar in softening characteristics to the control (unsterilized) rod. The peroxide sterilized rod may have been affected by the sterilization, as it seems to have softened at a somewhat slower rate. Since the peroxide sterilized sample softened more slowly, and had a shortened tensile elongation (Table 16), this suggests that the PVA may have been slightly crosslinked by the peroxide process.

The weight loss dissolution profiles of the same rod samples in 25° C. water was obtained. Again, the EtO and gamma sterilized rods were very similar to the unsterilized rod, but the peroxide sterilized rod was somewhat different. In this case, the peroxide sterilized rod lost weight more quickly than the other samples. This is the opposite of what would have been suspected from the DMA softening experiment above. It does appear that the rate of dissolution was very similar for all samples, but the peroxide rod lost more weight initially (a burst effect) before losing weight at about the same rate as the others.

Gamma and 1× EtO sterilized rod samples were completely issolved in tryptic soy agar and incubated for 48 hours. No bacterial growth was observed for any rod sample submitted. This implies that the gamma and 1× EtO sterilized samples were sterile both inside (bulk) and on the outside surface. It is expected that gamma would penetrate the rod bulk to sterilize the inside of the sample, but it is not known if the EtO would. If not, then apparently the extrusion temperature was extreme enough to destroy the bioburden activity in the bulk of the rods. No peroxide sterilized or unsterilized (control) rods were submitted for testing.

Example 6

In vitro hemocompatibility studies were carried out using unsterilized extruded AIRVOL 205 rods. The desired concentration of PVA was made by dissolving 5 mm rod pieces in PlasmaLyteA buffer solution. The 44 ppm PVA concentration was thought to be representative of the concentration of fully dissolved PVA in blood. The test was run with 1 ml of the PVA solution added to 9 ml heparinized (0.8 ppm) blood in a test tube, rocked at ambient temperature for 60 minutes. Table 17 shows the results of the hemocompatibility tests. Essentially, the PVA was hemocompatible except for some complement activation (elevated levels of SC5b9 complement marker), and possibly some platelet activation (BTG). It should be noted that only one replicate was run, and studies that are more rigorous are needed to better understand PVA's hemocompatibility. The PVA rod sample did not completely dissolve during this one-hour test.

TABLE 17

Preliminary hemocompatibility testing of dissolved AIRVOL 205 PVA rods.

| Sample | Donor | Hbg | Plt | WBC | TAT | SC5b9 | BTG | Elastase | PFHb |
|---|---|---|---|---|---|---|---|---|---|
| A avg | A | 13.9 | 248 | 5.2 | 15 | 20 | 123 | 27 | 8 |
| B avg | B | 15.0 | 173 | 6.2 | 3 | 20 | 245 | NA | NA |
| 0 ppm PVA | B | 14.7 | 75 | 5.5 | 9 | 294 | 1723 | NA | NA |
| 4.4 ppm PVA | A | 12.9 | 112 | 4.4 | 10 | 1402 | 905 | 5 | 11 |
| 44 ppm PVA | A | 13.1 | 166 | 4.5 | 20 | 2454 | 283 | 80 | 15 |
| 440 ppm PVA | B | 12.8 | 113 | 5.4 | 15 | 3767 | 673 | 23 | 11 |
| PVA rod | A | 18.5 | 110 | 3.9 | 24 | 1556 | 247 | 89 | 5 |

NA - data not available
Hgb - total hemoglobin (hemolysis)
Plt - platelet count (hemolysis)
WBC - white blood cell count (hemolysis)
TAT - thrombin - antithrombin III concentration (coagulation)
SC5b9 - complement complex concentration (complement activation)
BTG - beta thrombin globulin concentration (platelet activation)
Elastase - concentration (leukocyte activation)
PFHb - plasma free hemoglobin concentration (hemolysis)

Likely the major degradation mechanism of PVA would be any further hydrolysis of the vinyl acetate groups (on 12 mole % of the monomer units) to produce a vinyl alcohol group on the polymer and a molecule of acetic acid. There is a small chance that during extrusion processing conditions these same vinyl acetate groups may oxidize to release acetic acid and leave a C=C group in the polymer. It is thought that both mechanisms would be minor in degree.

For in vitro toxicity testing, acute toxicity was evaluated. The Acute Toxicity Phase I testing included: MEM Elution Cell Culture; Static Hemolysis (rabbit red blood cells); Systemic Injection (0.9% saline); Intracutaneous Injection (0.9% saline); Rabbit Pyrogen (0.9% saline). The actual PVA concentration used was 5,000 ppm (0.1 gram per 20 ml). This gives a safety factor of 125 (125×40 ppm=5,000 ppm). Traditionally, a safety factor of 100 is used for these types of studies. The PVA solution passed all of the tests.

The Acute Toxicity Phase 2 testing included: Sensitization Assay (guinea pig maximization test); Ames Mutagenicity; In Vitro Hemocompatibility (hematocrit, blood count, erythrocyte indices, platelet count, plasma hemoglobin); Complement activation (PVA rod in blood for 90 minutes at 37° C.); Complement activation (saline-dissolved PVA rod in blood for 90 minutes at 37° C.). The PVA passed all of the tests, except the complement activation of the fully dissolved PVA rod. Based on the study's criteria, the fully dissolved PVA induced complement activation of the C3a and SC5b9 proteins in human plasma as compared to untreated plasma and a "negative control plasma" (plasma exposed to the NaCl extract of a negative control plastic). However, the complement activation test containing a PVA rod (not a fully dissolved solution) did pass the test criteria. It was noted that the rod did not fully dissolve during the 90 minutes testing incubation time. The rod was probably ⅔ to ¾ dissolved, resulting in a lower PVA concentration.

It should be understood that the exemplary annuloplasty ring described herein and shown in the drawings represents only a presently preferred embodiment of the invention. Indeed, various modifications and additions may be made to such embodiment without departing from the spirit and scope of the invention. Thus, other modifications and additions may be obvious to those skilled in the art and may be implemented to adapt the present invention for use in a variety of different applications.

What is claimed is:

1. An annuloplasty device for implantation into a heart of a patient, comprising a band-shaped annuloplasty member having an initial modulus of elasticity of about 1 GPa or more, and a final modulus of elasticity of about 100 MPa or less after immersion in a biological environment, wherein the band-shaped member comprises a non-degradable structural component and a flexibilizing component differing from the structural component, and wherein the flexibilizing component is located within the structural component, wherein the band-shaped member has a final modulus of elasticity of about 100 MPa or less after immersion in a biological environment for no more than about 7 days.

2. The device of claim 1, wherein the flexibilizing component is a core flexibilizing component and the structural component completely envelopes the core flexibilizing component.

3. The device of claim 2, wherein the core flexibilizing component comprises poly(vinyl alcohol-co-vinyl acetate) or poly(vinyl pyrrolidone).

4. The device of claim 2, wherein the core flexibilizing component is in the form of a tube or rod.

5. An annuloplasty device for implantation into a heart of a patient, comprising a band-shaped member having an initial modulus of elasticity of about 1 GPa or more, and a final modulus of elasticity of about 100 MPa or less after immersion in a biological environment, wherein the band-shaped member comprises a non-degradable structural component and a flexibilizing component differing from the structural component, and wherein the flexibilizing component is located within the structural component, wherein the band-shaped member has a final modulus of elasticity of about 100 MPa or less after immersion in a biological environment for no more than about 3 days.

6. An annuloplasty device for implantation into a heart of a patient, comprising a band-shaped annuloplasty member having an initial modulus of elasticity of about 1 GPa or more, and a final modulus of elasticity of about 100 MPa or less after immersion in a biological environment, wherein the band-shaped member comprises a non-degradable structural component and a flexibilizing component differing from the structural component, and wherein the structural component has an external surface and the flexibilizing component is coated on at least a portion of the external surface of the structural component.

7. The device of claim 6, wherein the flexibilizing component is coated on the entire external surface of the structural component.

8. The device of claim 6, wherein the band-shaped member has a final modulus of elasticity of about 100 MPa or less after immersion in a biological environment for no more than about 7 days.

9. The device of claim 6, wherein the band-shaped member has a final modulus of elasticity of about 100 MPa or less after immersion in a biological environment for no more than about 3 days.

10. The device of claim 1 or claim 6, wherein the band-shaped member is substantially continuous.

11. The device of claim 1 or claim 6, wherein the band-shaped member is in the form of a closed ring.

12. The device of claim 1 or claim 6, wherein the band-shaped member is in the form of an open ring.

13. The device of claim 1 or claim 6, wherein the flexibilizing component changes modulus in a biological environment as a result of dissolution, biodegradation, plasticization, or phase transition.

14. The device of claim 1 or claim 6, further comprising a pharmaceutically active agent.

15. The device of claim 1 or claim 6, wherein the biological environment comprises the body of a human patient.

16. An annuloplasty device for implantation into a heart of a patient, comprising a band-shaped annuloplasty member having an initial modulus of elasticity of about 1 GPa or more, and a final modulus of elasticity of about 100 MPa or less after immersion in a biological environment for no more than about 7 days, wherein the band-shaped member comprises a non-degradable structural component and a flexibilizing component differing from the structural component and comprising poly(vinyl alcohol-co-vinyl acetate).

17. The device of claim 16, wherein the structural component completely envelopes the flexibilizing component.

18. The device of claim 16, wherein the band-shaped member has a final modulus of elasticity of about 100 MPa or less after immersion in a biological environment for no more than about 3 days.

19. The device of claim 16, wherein the poly(vinyl alcohol-co-vinyl acetate) has a molecular weight of about 15,000 to about 80,000.

20. The device of claim 16, wherein the poly(vinyl alcohol-co-vinyl acetate) is about 85% to about 90% hydrolyzed.

21. An annuloplasty device for implantation into a heart of a patient, comprising a band-shaped member having an initial modulus of elasticity of about 1 GPa or more, and a final modulus of elasticity of about 100 MPa or less after immersion in a biological environment for no more than about 7 days; wherein the band shaped member comprises a first outer non-degradable material surrounding a second, differing core material that softens after immersion in the biological environment.

22. The device of claim 21, wherein the band-shaped member comprises a core comprising a flexibilizing component surrounded by an outer sheath comprising a structural component.

23. The device of claim 22, wherein the flexibilizing component comprises poly(vinyl alcohol-co-vinyl acetate) or poly(vinyl pyrrolidone).

24. The device of claim 22, wherein the structural component comprises polyethylene terephthalate.

25. The device of claim 22, further comprising an inner perforated sheath surrounding the core.

26. The device of claim 25, wherein the inner perforated sheath comprises silicone.

27. An annuloplasty device for implantation into a heart of a patient, comprising a band-shaped annuloplasty member having an initial modulus of elasticity of about 1 GPa or more, and a final modulus of elasticity of about 100 MPa or less after immersion in a biological environment for no more than about 7 days, the device further comprising non-degradable structural means for providing support and flexibilizing means, differing from the structural means, for providing the change in modulus of elasticity after the immersion in the biological environment.

28. The device of claim 27, wherein the band-shaped member has a final modulus of elasticity of about 100 MPa or less after immersion in a biological environment for no more than about 3 days.

29. The device of claim 27, wherein the band-shaped member is substantially continuous.

30. The device of claim 27, wherein the flexibilizing means comprises a core component and the structural means completely envelopes the core component.

31. The device of claim 30, wherein the core component comprises poly(vinyl alcohol-co-vinyl acetate) or poly(vinyl pyrrolidone).

32. The device of claim 31, wherein the core component is in the form of a tube or rod.

33. The device of claim 27, wherein the flexibilizing means comprises a component that changes modulus in a biological environment as a result of dissolution, biodegradation, plasticization, or phase transition.

34. The device of claim 27, further comprising a pharmaceutically active agent.

35. The device of claim 27, wherein the biological environment comprises the body of a human patient.

36. An annuloplasty device for implantation into a heart of a patient, comprising a band-shaped annuloplasty member having an initial modulus of elasticity of about 1 GPa or more, and a final modulus of elasticity of about 100 MPa or less after immersion in a biological environment, the device comprising non-degradable structural means for providing support and flexibilizing means differing from the structural means, for providing a change in modulus of elasticity after immersion in a biological environment, wherein the flexibilizing means is impregnated in the structural means.

37. An annuloplasty device for implantation into a heart of a patient, comprising a band-shaped annuloplasty member having an initial modulus of elasticity of about 1 GPa or more, and a final modulus of elasticity of about 100 MPa or less after immersion in a biological environment, the device comprising non-degradable structural means for providing support and flexibilizing means differing from the structural means, for providing a change in modulus of elasticity after immersion in a biological environment, wherein the structural means has an external surface and the flexibilizing means is coated on at least a portion of the external surface of the structural means.

38. The device of claim 37, wherein the flexibilizing means is coated on the entire external surface of the structural means.

* * * * *